United States Patent [19]

Mazanek et al.

[11] 4,293,680

[45] Oct. 6, 1981

[54] PROCESS FOR THE PRODUCTION OF DIISOCYANATO TOLUENE MIXTURES HAVING AN INCREASED CONTENT OF 2,6-DIISOCYANATO TOLUENE, AND THE USE THEREOF AS SYNTHESIS COMPONENTS IN THE PRODUCTION OF POLYURETHANE ELASTOMERS

[75] Inventors: Jan Mazanek, Munich; Hanns P. Nüller, Odenthal, both of Fed. Rep. of Germany

[73] Assignee: Bayer Aktiengesellschaft, Leverkusen, Fed. Rep. of Germany

[21] Appl. No.: 175,601

[22] Filed: Aug. 6, 1980

[30] Foreign Application Priority Data

Aug. 8, 1979 [DE] Fed. Rep. of Germany ....... 2932095

[51] Int. Cl.$^3$ .............................................. C08G 18/76
[52] U.S. Cl. ...................................... 528/67; 252/182; 260/453 SP; 544/193
[58] Field of Search .................. 260/453 SP; 252/182; 528/67; 544/193

[56] References Cited

U.S. PATENT DOCUMENTS

| | | | |
|---|---|---|---|
| 3,022,328 | 2/1962 | Cobb | 260/453 SP |
| 3,217,024 | 11/1965 | Park et al. | 260/453 SP |
| 3,316,285 | 4/1967 | Cleveland | 260/453 |
| 3,554,872 | 1/1971 | Chang et al. | 260/453 SP |
| 3,620,929 | 11/1971 | Kober et al. | 260/453 SP |
| 3,652,424 | 3/1972 | Jackson et al. | 252/182 |
| 4,115,373 | 9/1978 | Henes et al. | 260/453 P |

*Primary Examiner*—Maurice J. Welsh
*Attorney, Agent, or Firm*—Gene Harsh; Joseph C. Gil

[57] ABSTRACT

The instant invention is directed to a process for the production of diisocyanate mixtures of 2,4-diisocyanato toluene and 2,6-diisocyanato toluene, having from 36 to 90% by weight, based on the total mixture, of 2,6-diisocyanato toluene, comprising: trimerizing some of the isocyanate groups of a diisocyanate mixture of 2,4-diisocyanato toluene and 2,6-diisocyanato toluene, having a maximum content of 2,6-diisocyanato toluene of 35% by weight based on the total mixture and isolating from the reaction mixture which is thus obtained, a diisocyanate mixture having an increased content of 2,6-diisocyanato toluene.

The invention is also directed to the use of these mixtures as synthesis components in the production of polyurethane elastomers.

5 Claims, No Drawings

PROCESS FOR THE PRODUCTION OF DIISOCYANATO TOLUENE MIXTURES HAVING AN INCREASED CONTENT OF 2,6-DIISOCYANATO TOLUENE, AND THE USE THEREOF AS SYNTHESIS COMPONENTS IN THE PRODUCTION OF POLYURETHANE ELASTOMERS

BACKGROUND OF THE INVENTION

The present invention relates to a new process for the production of mixtures of 2,4- and 2,6-diisocyanato toluene, which are characterized by an especially high content of 2,6-diisocyanato toluene. The present invention is also directed to the use of these mixtures as synthesis components in the production of polyurethane elastomers.

Diisocyanato toluenes or tolylene diisocyanates (abbreviated to "TDI") are commercially and economically extremely important starting materials for the large scale production of polyurethane synthetic materials. They are obtained on a large scale by phosgenation of the corresponding diamino toluenes or tolylene diamines (abbreviated to "TDA"). Until now, "TDI 100," "TDI 80," and "TDI 65" that is, respectively, pure 2,4-diisocyanato toluene, its mixture having 20% of 2,6-diisocyanato toluene, and its mixture having 35% of 2,6-diisocyanato toluene, based on the total mixture have, in particular, played a major commercial role.

TDI having a content of more than 35% by weight of 2,6-diisocyanato toluene is already known. Thus, for example, U.S. Pat. No. 3,022,328 describes the partial reaction of TDI 65 with tertiary alcohols and the isolation by distillation of the tolylene diisocyanate isomer mixture having an increased concentration of 2,6-diisocyanato toluene from the reaction product obtained. According to U.S. Pat. No. 3,554,872, an analogous concentration of the 2,6-isomer results from the partial reaction of TDI with polyester polyols or polyether polyols and by the subsequent distillative working up of the reaction product.

As was found, the production of diisocyanato toluene isomer mixtures having a content of from 36 to 90%, preferably from 45 to 85% by weight of 2,6-diisocyanato toluene from diisocyanato toluene isomer mixtures having a maximum content of 35% by weight of 2,6-diisocyanato toluene can be carried out, in a particularly simple way, by the partial trimerization of the isocyanate groups of the initial mixture and by the subsequent isolation of the unconverted diisocyanate having an increased concentration of 2,6-diisocyanato toluene.

It was also found that the diisocyanato toluene isomer mixtures which can thus be obtained or according to any processes of the prior art, having a 2,6-diisocyanato toluene content particularly of from 45% to 85% by weight using conventional higher molecular polyhydroxyl compounds of polyurethane chemistry and chain lengthening agents can also be processed into high grade polyurethane elastomers, when simple glycols are used as chain lengthening agents instead of conventional diamines. Until now, the production of high grade polyurethane elastomers from TDI, higher molecular polyols and low molecular glycols as chain lengthening agents was not possible. Instead, until now, in order to produce elastomers of this kind, either expensive and often physiologically harmful diamine chain lengthening agents or special diisocyanates (for example, 1,5-diisocyanato naphthalene) had to be used in order to produce polyurethane elastomers having mechanical properties which met the requirements of industrial practice.

DESCRIPTION OF THE INVENTION

Accordingly, the present invention relates to a process for the production of diisocyanate mixtures of 2,4-diisocyanato toluene and 2,6-diisocyanato toluene, having from 36 to 90%, preferably from 45 to 85% by weight, based on the total mixture, of 2,6-diisocyanato toluene, comprising: trimerizing some of the isocyanate groups of a diisocyanate mixture of 2,4-diisocyanato toluene and 2,6-diisocyanato toluene, having a maximum content of 2,6-diisocyanato toluene of 35% by weight based on the total mixture and isolating from the reaction mixture which is thus obtained, a diisocyanate mixture having an increased content of 2,6-diisocyanato toluene.

The present invention also relates to a process for the production of polyurethane elastomers comprising: reacting an organic polyisocyanate with a higher molecular weight polyhydroxyl compound and a low molecular weight chain lengthening agent in a one or two stage process, the improvement wherein
(a) said organic polyisocyanate is a diisocyanate mixture of 2,4-diisocyanato toluene and 2,6-diisocyanato toluene, having a 2,6-diisocyanato toluene content of from 36 to 90%, preferably from 45 to 85% by weight, based on the total mixture, and
(b) said chain lengthening agent is an aliphatic glycol which optionally contains ether bridges, having a molecular weight in the range of from 62 to 200.

The starting materials for the process according to the present invention for the production of the isomer mixtures having a high concentration of 2,6-diisocyanato toluene are diisocyanate mixtures of 2,4-diisocyanato toluene and 2,6-diisocyanato toluene, having a maximum 2,6-diisocyanato toluene content of 35% by weight, based on the total mixture. Preferred starting materials are those mixtures having a content of 2,6-diisocyanato toluene of 20 or 35% by weight based on the total mixture. As the starting material for the process according to the present invention, diisocyanato toluene mixtures are preferably used which contain at least 99% by weight, based on the total mixture of the named isomers.

To carry out the trimerization of some isocyanate groups of the diisocyanate starting material, the methods which are known for the trimerization of organic diisocyanates are used as they are principally described, for example, in "Polyurethanes," I., Interscience Publishers (1962), pages 94 to 97. Here as well, any catalysts which can be deactivated thermally or by catalyst poisons, can be used. Suitable catalysts include tertiary phosphines, for example, tributyl phosphine, while sulfur is an example of a suitable catalyst poison (British Pat. No. 1,244,416 or German Auslegeschrift No. 1,954,093). The reaction is carried out at an elevated temperature, for example, at from 30° to 150° C., preferably from 50° to 120° C. The use of an auxiliary solvent, for example, ethylacetate or butylacetate can be advantageous. As is described in Example 3 of German Auslegeschrift No. 1,954,093, after the reaction has finished, small quantities of unconverted sulfur can be removed by filtration after which, the reaction mixture is subjected to distillation.

Equally suitable catalysts are, for example, the catalysts of German Offenlegungsschrift No. 2,551,634 (U.S. Pat. No. 4,115,373 which is herein incorporated by reference). The Mannich base which can be obtained by the condensation of 2 moles of phenol with 4 moles of methylamine and approximately 5.5 moles of formaldehyde according to Example 1 of U.S. Pat. No. 4,115,373 is particularly suitable for use in the process according to the present invention. The trimerization reaction is carried out at a temperature in the range of from approximately 30° to 150° C., preferably of from 30° to 100° C. The reaction may be stopped by either the addition of a catalyst poison, for example, toluene sulfonic acid methyl ester, or by heating the reaction mixture to approximately to 110°–150° C., preferably 110°–120° C. which results in the thermal decomposition of the catalyst. Here, as well, the use of an auxiliary solvent, for example, ethylacetate or butylacetate, can be expedient. The trimerization reaction can also, however, be substantially carried to completion. The trimerization catalysts are preferably used in an amount of from 0.01 to 3% by weight based on diisocyanato toluene isomer mixture. It is often advisable to add a very small amount of an acidic substance such as benzoyl chloride to the starting diisocyanate mixture to neutralize any trace of basic substances which might act as catalyst for side reactions.

The process according to the present invention is generally interrupted after a trimerization of from 5 to 45%, preferably from 10 to 40% of the isocyanate groups present in the initial mixture. The unchanged diisocyanate is then isolated from the reaction mixture, for example, by extraction or preferably distillation. The question as to how far the trimerization reaction is carried out naturally depends on the content of the initial mixture of 2,6-diisocyanato toluene and on the isomer content which is desired in the product of the process. The products of the process according to the present invention are of from 36 to 90%, preferably from 45 to 85% by weight of 2,6-diisocyanato toluene and from 10 to 64%, preferably from 15 to 55% by weight of 2,4-diisocyanato toluene.

In the process according to the present invention for the production of polyurethane elastomers, the diisocyanato toluene isomer mixtures which are obtained thus, or according to any other processes, of the described composition are reacted with higher molecular weight polyhydroxyl compounds and selected chain lengthening agents.

Suitable higher molecular weight hydroxyl compounds are polyesters, polyethers, polythioethers, polyacetals, polycarbonates and polyester amides having from 2 to 4, preferably 2 or 3, in particular 2 hydroxyl groups, having a low melting point. These polyhydroxyl compounds generally have a molecular weight of from 400 to 10,000, preferably from 800 to 6000 and have a melting point below 60° C., preferably below 40° C., particularly below 30° C. The corresponding polyesters, polyethers or polycarbonates having hydroxyl groups are preferred.

Suitable polyesters having hydroxyl groups are, for example, reaction products of multifunctional preferably difunctional, and optionally additionally trifunctional, alcohols with multibasic, preferably dibasic carboxylic acids. Instead of the free polycarboxylic acids, the corresponding polycarboxylic acid anhydrides or corresponding polycarboxylic acid ester of low alcohols or mixtures thereof can be used for the production of polyesters. The polycarboxylic acids can be aliphatic, cycloaliphatic, aromatic, and/or heterocyclic. They can be optionally substituted, e.g., by halogen atoms, and/or can be unsaturated. Examples of these are adipic acid, phthalic acid, and isophthalic acid.

The following are suitable as multifunctional alcohols, ethylene glycol, (1,2)- and (1,3)-propylene glycol, (1,4)- and (2,3)-butylene glycol, (1,6)-hexanediol, (1,8)-octanediol, neopentyl, glycol, cyclohexane dimethanol (1,4-bis-(hydroxymethyl)-cyclohexane), 2-methyl-1,3-propanediol, glycerine or trimethylol propane.

The polyethers having hydroxyl groups are produced, e.g., by the polymerization of an epoxide such as ethylene oxide, propylene oxide, butylene oxide, tetrahydrofuran, styrene oxide or epichlorohydrin by itself (e.g., in the presence of $BF_3$) or by the addition of these epoxides (optionally in admixture or subsequently) with starter components having reactive hydrogen atoms. Examples of starter components having reactive hydrogen atoms include water, alcohols, ammonia or amines, e.g., ethylene glycol, (1,3)- or (1,2)-propylene glycol, trimethylolpropane, 4,4'-dihydroxydiphenylpropane, aniline, ethanolamine or ethylene diamine. Polyethers having predominantly (up to 90% by weight based on all the OH-groups present in the polyether) primary OH-groups are preferred. Also suitable are polyethers modified by vinyl polymers, which may be obtained, for example, from the polymerization of styrene and acrylonitrile in the presence of polyethers (U.S. Pat. Nos. 3,383,351, 3,304,273, 3,523,093, 3,110,695 and German Pat. No. 1,152,536).

Representatives of these compounds which may be used according to the present invention are described, for example, in *High Polymers,* Vol. XVI, "Polyurethanes, Chemistry and Technology," by Saunders-Frisch, Interscience Publishers, New York, London, Vol. I, 1962, pages 32–42 and pages 44–54 and Vol. II, 1964, pages 5–6 and 198–199, also in Kunststoff Handbuch, VII, Vieweg-Höchtlen, Carl-Hanser-Verlag, Munich, 1966, e.g., on pages 45–71. Mixtures of the above-mentioned compounds, e.g., mixtures of polyethers and polyesters, may also be used.

Polyhydroxyl compounds can also be used which contain high molecular polyadducts or polycondensates in a finely dispersed or dissolved form. Modified polyhydroxyl compounds of this kind are obtained if polyaddition reactions (e.g., reactions between polyisocyanates and amino functional compounds) or polycondensation reactions (e.g., between formaldehyde and phenols and/or amines) are allowed to take place directly in situ in the above-mentioned compounds having hydroxyl groups. Processes of this kind are described, for example, in German Auslegeschriften Nos. 1,168,075 and 1,260,142 and German Offenlegungsschriften Nos. 2,324,134; 2,423,984; 2,512,385; 2,513,815; 2,550,796; 2,550,797; 2,550,833 and 2,550,862. It is also possible according to U.S. Pat. No. 3,869,413 or German Offenlegungsschrift No. 2,550,860 to mix a finished aqueous polymer dispersion with a polyhydroxyl compound with subsequent removal of water from the mixture.

Polycarbonates having hydroxyl groups are also suitable. These can be produced, for example, by the reaction of diols (such as (1,3)-propanediol, (1,4)-butanediol, and/or (1,6)-hexanediol, diethylene glycol, triethylene glycol or tetraethylene glycol) with diaryl carbonates (e.g., diphenyl carbonate) or with phosgene.

In the process according to the present invention for the production of polyurethane elastomers any aliphatic glycols (optionally interrupted by ether bridges), having a molecular weight in the range of from 62 to 200 are suitable as chain lengthening agents. The following are mentioned as examples of compounds of this kind, ethylene glycol (1,2)- and (1,3)-propylene glycol, (1,4)- and (2,3)-butylene glycol, (1,5)-pentanediol, (1,4)-butanediol, (1,6)-hexanediol, neopentyl glycol, diethylene glycol, triethylene glycol, dipropylene glycol, tripropylene glycol, dibutylene glycol or tributylene glycol. Mixtures of the mentioned chain lengthening agents can naturally also be used.

The process according to the present invention for the production of polyurethane elastomers can be carried out in one or two stages. In the production of polyurethane elastomers according to the one stage process, the diisocyanates, essential in the present invention, are reacted with a mixture of a higher molecular polyhydroxyl compound and a chain lengthening agent. The quantitative ratios of the reaction components are thereby selected in such a way that for each mole of higher molecular weight polyhydroxyl compound, from 0.5 to 7, preferably from 1 to 3 moles of the chain lengthening agent are present. The NCO/OH-equivalent ratio is preferably from 0.8 to 2, and most preferably from 0.9 to 1.3, based on all the isocyanate groups and all the hydroxyl groups. The reaction according to the one stage process generally takes place in the absence of a solvent at from 80° to 150°, preferably from 90° to 120° C.

In carrying out the process according to the present invention for the production of polyurethane elastomers according to the two stage process, an NCO-prepolymer is first produced from the diisocyanate and the higher molecular weight polyhydroxyl compound at from 70° to 140° C., preferably from 90° to 120° C. The reaction components are used in a quantity which corresponds to an NCO/OH-equivalent ratio of from 1.5 to 6, preferably from 2 to 4. The chain lengthening reaction takes place subsequently by the addition of the chain lengthening agent to the thus obtained NCO-prepolymer. The amount of the chain lengthening agent being such that, based on the NCO-groups of the NCO-prepolymers and hydroxyl groups of the chain lengthening agents, the NCO/OH-equivalent ratio is from 0.8 to 2, preferably from 0.9 to 1.3. The chain lengthening reaction is generally carried out at a temperature in the range of from 80° to 150°, preferably from 90° to 120° C. Catalysts are often also used in the production of polyurethane elastomers. Other catalysts which are also suitable are those of the known type, e.g., tertiary amines, such as triethylamine, 1,4-diazabicyclo-(2,2,2)-octane, aminoethyl piperazine or N,N-dimethyl benzylamine.

According to the present invention, it is also possible to use organometallic compounds, particularly organo tin compounds, as catalysts. The following are preferred organo tin compounds: tin(II)-salts or carboxylic acids (such as tin(II)-acetate, tin(II)-octoate, tin(II)-ethylhexoate and tin(II)-laurate) and tin(IV)-compounds (e.g., dibutyl tin oxide, dibutyl tin dichloride, dibutyl tin diacetate, dibutyl tin dilaurate, dibutyl tin maleate or dioctyl tin diacetate). All the above-mentioned catalysts can be used as mixtures.

Additional representatives of catalysts which may be used for the production of elastomers as well as information about the action of the catalysts are described in Kunststoff Handbuch, Vol. VII, published by Vieweg and Höchtlen, Carl-Hanser-Verlag, Munich, 1966, e.g., on pages 96 to 102.

Generally, the catalysts for the production of elastomers are used in a quantity of between approximately 0.001 and 10% by weight, based on the quantity of polyol.

According to the present invention, reaction retarders can also be used. Examples include acidic substances (such as hydrochloric acid) or acidic organic halides. Flame-proofing agents (e.g., tris-chloroethyl phosphate, tricresyl phosphate or ammonium phosphate and ammonium polyphosphate), stabilizers against ageing and atmospheric influences, softeners and fungistatic and bacteriostatic substances, and fillers (such as barium sulphate, kieselguhr, carbon black or whiting) may also be used.

Examples of auxiliary substances and additional substances which may optionally be used according to the present invention, as well as details about the method of application and action of these additional agents are described in the Kunststoff Handbuch, Vol. VII, published by Vieweg and Höchtlen, Carl-Hanser-Verlag, Munich, 1966, e.g., on pages 103–113.

The polyurethane elastomers which can be obtained according to the process of the present invention are distinguished by excellent mechanical characteristics in spite of the use of diisocyanato toluene, as the polyisocyanate component, and at the same time, the use of single glycols as chain lengthening agents.

The following examples are intended to describe the invention in more detail without limiting it.

In the production examples for the diisocyanate mixtures having an increased concentration of 2,6-isomers, initial mixtures having a content of 2,4- and 2,6-diisocyanato toluene of at least 99% by weight are used. All percentage figures relate to percent by weight.

EXAMPLE 1

730 g of tolylene diisocyanate (80% 2,4-isomer and 20% 2,6-isomer) and 0.7 g of benzoyl chloride were heated to 80° C. under a nitrogen atmosphere. 2.4 g of the Mannich base according to Example 1 of U.S. Pat. No. 4,115,373 (55% mixture) were added, the reaction temperature rising to 105° C. within approximately 10 minutes. It was then heated while being stirred for 50 minutes at 110° C. and then for five minutes at 120° C. After subsequent vacuum distillation, 138 g (18.9% of the theoretical yield based on the initial mixture) of tolylene diisocyanate (45% 2,6-isomer, 55% 2,4-isomer) were obtained. The residue (588 g, 80.5% of the theoretical yield) had an NCO-content of 23.1% and consisted predominantly of trimerized tolylene diisocyanate.

EXAMPLE 2

1800 g of tolylene diisocyanate (65% 2,4-isomer, 35% 2,6-isomer) and 1.75 g of benzoyl chloride were heated to 80° C. under a nitrogen atmosphere. 5.9 g of the Mannich base according to Example 1 of U.S. Pat. No. 4,115,373 (55% of the mixture) were added, the reaction temperature rising to 90° C. within approximately 10 minutes. It was then stirred for 1 hour at 90° C. and subsequently heated while being stirred for 5 minutes at 120° C. After subsequent vacuum distillation, 612 g (34% of the theoretical yield based on the initial mixture) of tolylene diisocyanate (51.5% 2,6-isomer, 48.5% 2,4-isomer) were obtained. The residue (1188 g, 66% of the theoretical yield) had an NCO-content of 21.6% and consisted predominantly of trimerized tolylene diisocyanate.

EXAMPLE 3

The process was carried out as described in Example 2, except that the mixture was stirred for 2 hours at 90° C. Yield (distillate): 387 g (21.5% of the theoretical yield based on the initial mixture) of tolylene diisocyanate (59.5% 2,6-isomer, 40.5% 2,4-isomer) yield (residue): 1413 g (78.5% of the theoretical yield).

EXAMPLE 4

The process was carried out as described in Example 2, except that the temperature rose to 90° C. within 30 minutes and the mixture was then stirred at 90° C. for 10 minutes. Yield (distillate): 135 g (7.5% of the theoretical yield based on the initial mixture) of tolylene diisocyanate (70% 2,6-isomer, 30% 2,4-isomer). Yield (residue): 1665 g (92.5% of the theoretical yield).

EXAMPLE 5

250 g (0.125 mole) of a polyether polyol of propylene oxide and ethylene oxide (9:1, mole/mole) having an average molecular weight of 2000 were dehydrated under vacuum for 30 minutes at 120° C. At 120° C., 65.3 g (0.375 mole) of tolylene diisocyanate (70% 2,6-isomer, 30% 2,4-isomer) were added, stirred for 10 minutes, then 3 drops of tin(II)-octoate were added and continually stirred for 20 minutes at 120° C. Subsequently, 21.8 g (0.245 mole) of (1,4)-butanediol were added, the mixture was stirred for 30 seconds and was poured onto a tray (200×200×60 mm) which was previously heated to 100° C.

After tempering for 24 hours at 100° C., an elastomer was obtained having the following characteristics:

| $\delta$100 | 1.9 MPa | (DIN 53504) |
|---|---|---|
| Tensile strength | 4.5 MPa | (DIN 53504) |
| Structural strength | 110 N | (DIN 53504) |
| Hardness | 73 ShA | (DIN 53505) |
| Elasticity | 43% | (DIN 53512) |

EXAMPLE 6

250 g (0.125 mole) of a polyester polyol of adipic acid, ethylene glycol and (1,4)-butanediol (7:3, mole/mole) having an average molecular weight of 2000 were dehydrated in a vacuum for 30 minutes at 120° C. At 120° C., 65.3 g of the diisocyanate mixture according to Example 2 were added and stirred for 30 minutes. Then 3 drops of tin(II)-octoate and 21.5 g (0.119 mole) of (1,4)-butanediol were added, the mixture was stirred for 30 seconds and was poured onto a tray (200×200×60 mm) which was previously heated to 100° L C. After tempering for 24 hours at 100° C., an elastomer having the following characteristics was obtained:

| $\delta$100 | 0.9 MPa | (DIN 53504) |
|---|---|---|
| Tensile Strength | 2.4 MPa | (DIN 53504) |
| Structural strength | 85 N | (DIN 53504) |
| Hardness | 62 ShA | (DIN 53505) |
| Elasticity | 37% | (DIN 53512) |

EXAMPLE 7

The process was carried out as described in Example 6, except that instead of using the specified tolylene diisocyanate mixture, a tolylene diisocyanate mixture containing 80% of the 2,6-isomer and 20% of the 2,4-isomer was used. The elastomer obtained had the following characteristics:

| $\delta$100 | 2.6 MPa | (DIN 53504) |
|---|---|---|
| Tensile strength | 9.5 MPa | (DIN 53504) |
| Structural strength | 181 N | (DIN 53504) |
| Hardness | 74 ShA | (DIN 53505) |
| Elasticity | 43% | (DIN 53512) |

Comparative Example

The process was carried out as described in Example 7, except that instead of using the specified tolylene diisocyanate mixture, a tolylene diisocyanate mixture ("TDI 80") containing 80% of the 2,4-isomer and 20% of the 2,6-isomer was used. The elastomer obtained had the following characteristics:

| $\delta$100 | 0.3 MPa | (DIN 53504) |
|---|---|---|
| Tensile strength | 0.4 MPa | (DIN 53504) |
| Structural strength | 33 N | (DIN 53504) |
| Hardness | 29 ShA | (DIN 53505) |
| Elasticity | 18 | (DIN 53512) |

What is claimed is:

1. A process for the production of diisocyanate mixtures of 2,4-diisocyanato toluene and 2,6-diisocyanato toluene, having from 36 to 90% by weight, based on the total mixture, of 2,6-diisocyanato toluene, comprising: trimerizing some of the isocyanate groups of a diisocyanate mixture of 2,4-diisocyanato toluene and 2,6-diisocyanato toluene, having a maximum content of 2,6-diisocyanato toluene of 35% by weight based on the total mixture and isolating from the reaction mixture which is thus obtained, a diisocyanate mixture having an increased content of 2,6-diisocyanato toluene.

2. The process of claim 1, wherein said 2,6-diisocyanato toluene is present in the reaction mixture thus obtained in an amount of from 45 to 85%.

3. The process of claim 1, wherein said starting diisocyanate mixture contains at least 99% by weight of 2,4- and 2,6-diisocyanato toluene.

4. In a process for the production of polyurethane elastomers comprising: reacting an organic polyisocyanate with a higher molecular weight polyhydroxyl compound and a chain lengthening agent in a one stage or two stage process, the improvement wherein
    (a) said organic polyisocyanate is a diisocyanate mixture of 2,4-diisocyanato toluene and 2,6-diisocyanato toluene, having from 36 to 90% by weight, based on the total mixture, of 2,6-diisocyanato toluene and
    (b) said chain lengthening agent is an aliphatic glycol which optionally contains ether bridges, having a molecular weight in the range of from 62 to 200.

5. The process of claim 4, wherein said 2,6-diisocyanato toluene is present in said diisocyanate mixture in an amount of from 45 to 85%.

* * * * *